(12) United States Patent
Akita et al.

(10) Patent No.: US 9,702,067 B2
(45) Date of Patent: Jul. 11, 2017

(54) MANUFACTURING METHOD FOR HEART CORRECTION NET

(71) Applicants: KANAZAWA MEDICAL UNIVERSITY, Uchinada-machi, Kahoku-gun, Ishikawa (JP); Kanazawa Institute of Technology, Nonoichi-shi, Ishikawa (JP); Tokai Medical Products, Inc., Kasugai-shi, Aichi (JP)

(72) Inventors: Toshiaki Akita, Uchinada-machi (JP); Masashi Yamabe, Nonoichi-shi (JP); Masahiro Seto, Nonoichi-shi (JP); Toru Suzuki, Nonoichi-shi (JP); Naoyuki Takesue, Hino-shi (JP)

(73) Assignees: Kanazawa Medical University, Ishikawa (JP); Kanazawa Institute of Technology, Ishikawa (JP); Tokai Medical Products, Inc., Aichi (JP)

( * ) Notice: Subject to any disclaimer, the term of this patent is extended or adjusted under 35 U.S.C. 154(b) by 468 days.

(21) Appl. No.: 14/383,919

(22) PCT Filed: Mar. 8, 2013

(86) PCT No.: PCT/JP2013/056513
§ 371 (c)(1),
(2) Date: Sep. 9, 2014

(87) PCT Pub. No.: WO2013/133426
PCT Pub. Date: Sep. 12, 2013

(65) Prior Publication Data
US 2015/0020547 A1    Jan. 22, 2015

(30) Foreign Application Priority Data
Mar. 9, 2012  (JP) ................................ 2012-053366

(51) Int. Cl.
*G06K 9/00* (2006.01)
*D04B 15/66* (2006.01)
(Continued)

(52) U.S. Cl.
CPC .............. *D04B 15/66* (2013.01); *A61B 17/00* (2013.01); *A61F 2/2481* (2013.01);
(Continued)

(58) Field of Classification Search
None
See application file for complete search history.

(56) References Cited

U.S. PATENT DOCUMENTS 7,174,896 B1 *  2/2007  Lau ..................... A61F 2/2481
                                                    128/898
7,871,366 B2     1/2011  Criscione et al.
(Continued)

FOREIGN PATENT DOCUMENTS

JP    2003532489    11/2003
JP    4582549       11/2010
(Continued)

OTHER PUBLICATIONS

International Preliminary Report on Patentability for Application No. PCT/JP2013/056513 dated Sep. 12, 2014.
(Continued)

*Primary Examiner* — Matthew Bella
*Assistant Examiner* — Jose M Torres
(74) *Attorney, Agent, or Firm* — Jenkins, Wilson, Taylor & Hunt, P.A.

(57) ABSTRACT

A manufacturing method of a heart correction net is provided. The method includes: a first step of taking cross-sectional images of a heart in a layer direction, in which an apex and a base of the heart are connected; a second step of extracting outlines of the heart from the cross-sectional
(Continued)

images; a third step of defining dividing points with respect to a three-dimensional shape reconstructed based on the outlines, the dividing points being defined on the outlines in a circumferential direction of the heart; a fourth step of dividing a contour of the heart in three-dimensions into divided regions based on the plurality of the dividing points, and creating development data, in which the each of the divided regions is developed on a two-dimensional plane, while an approximate shape of each of the divided regions is maintained; a fifth step of creating paper-pattern data based on the development data; and a sixth step of knitting the heart correction net with a knitting machine based on the paper-pattern data.

4 Claims, 8 Drawing Sheets

(51) Int. Cl.
*A61F 2/24* (2006.01)
*A61B 17/00* (2006.01)
*G06F 19/00* (2011.01)
*A61B 34/10* (2016.01)

(52) U.S. Cl.
CPC ........... *A61B 2017/00526* (2013.01); *A61B 2034/108* (2016.02); *A61F 2240/002* (2013.01); *G06F 19/3437* (2013.01)

(56) References Cited

U.S. PATENT DOCUMENTS

| | | | |
|---|---|---|---|
| 2002/0045800 A1* | 4/2002 | Lau | A61F 2/2481 600/37 |
| 2004/0176658 A1* | 9/2004 | McMurray | A61F 2/2481 600/37 |
| 2008/0033235 A1 | 2/2008 | Shapland et al. | |
| 2011/0196196 A1 | 8/2011 | Shapland et al. | |
| 2014/0107405 A1* | 4/2014 | Hjelle | A61M 1/107 600/37 |
| 2014/0107775 A1* | 4/2014 | Hjelle | A61M 1/107 623/3.21 |

FOREIGN PATENT DOCUMENTS

| | | |
|---|---|---|
| JP | 2010535081 | 11/2010 |
| WO | WO 2013/133426 | 9/2013 |

OTHER PUBLICATIONS

International Search Report for Application No. PCT/JP2013/056513 dated Apr. 9, 2013.
Japanese Office Action for Application No. 2012-053366 dated Jan. 26, 2016.

* cited by examiner

MANUFACTURING METHOD FOR HEART CORRECTION NET

CROSS-REFERENCE TO RELATED APPLICATIONS

The present application is filed under the provisions of 35 U.S.C. §371 and claims the priority of International Patent Application No. PCT/JP2013/056513 filed on Mar. 8, 2013 and of Japanese Patent Application No. 2012-53366 filed on Mar. 9, 2012 The disclosures of the foregoing international patent application and Japanese patent application are hereby incorporated by reference herein in their respective entireties.

TECHNICAL FIELD

The present invention relates to a manufacturing method for a heart correction net that is externally fitted to the outside of a heart for cardiac disease treatment.

BACKGROUND ART

As one of the medical instruments for treating cardiac disease, a heart correction net that is fitted to the outside of a heart has been proposed (see, for example, Patent Document 1). This heart correction net is formed with a mesh-structured fabric into a cup-like shape. Such heart correction net is fitted to the outside of a heart of a patient with cardiac failure in order to inhibit further cardiac dilatation (cardiac remodeling) and to prevent deterioration of cardiac failure.

In case of the heart correction net disclosed in Patent Document 1, the net is configured based on the size of a relatively large heart so that the net can be fitted to a heart irrespective of the size thereof. Due to such configuration, an excess portion of the net needs to be removed while in surgery according to the size of the patient's heart, and, subsequently, the portion from which the excess portion is removed needs to be sutured.

Meanwhile, if the removal amount of the excess portion is insufficient, the heart correction net may become too large for the heart. In this case, the effect to inhibit cardiac dilatation becomes deficient. On the other hand, if the removal amount is unnecessarily large, the heart correction net may become too small for the heart, which may cause diastolic dysfunction. Therefore, the removal amount has to be appropriately determined. However, since no standard has been available regarding the removal amount, decisions have been left to surgeons' subjective views. This has been causing variation in treatment results. Moreover, removal and suture procedures require time, which places a burden on patients as much as the length of the time the procedures take.

In order to solve these problems, the inventors of the present case have proposed a technique, in which patients' hearts that are individually different in sizes and shapes are actually three-dimensionally measured, and heart correction nets are knitted so as to have the configurations that snugly conform to patients respectively (see Patent Document 2). In this technique, with a tomographic apparatus, such as CT (Computed Tomography), an MRI (Magnetic Resonance Imaging), and an echocardiographic apparatus, cross-sectional images of a heart are measured. A contour of the heart (two-dimensional data) is extracted from each of the cross-sectional images. Based on the contours from the plurality of the cross-sectional images, three-dimensional data is created. Paper-pattern data, created based on the three-dimensional data, is inputted into a computerized knitting machine that is capable of multidimensional knitting. As a result, a heart correction net is produced so as to snugly conform to a patient's heart.

The heart correction net, manufactured with such technique, is fitted to a heart only by covering. Unlike a large general-purpose heart correction net, an unnecessary portion of the net does not have to be removed in a surgery in order to adjust the heart correction net to the size of a patient's heart. Therefore, surgery can be performed faster for not removing the unnecessary portion, which can considerably shorten surgical time and reduce the burden on patients.

PRIOR ART DOCUMENTS

Patent Documents

Patent Document 1: Publication of Unexamined Japanese Patent Application No. 2003-532489
Patent Document 2: Publication of Japanese Patent No. 4582549

SUMMARY OF THE INVENTION

Problems to be Solved by the Invention

However, the three-dimensional shape of a heart is complicated. In an attempt to highly precisely reproduce the contour of a heart with a heart correction net according to the above-mentioned Patent Document 2, the paper-pattern data, which is necessary when the heart correction net is knitted, is likely to become excessively complicated. In such case, creating the paper-pattern data becomes difficult and requires additional work, which consequently increases the manufacturing cost of the heart correction net.

One possible way to avoid such problems is to simplify the shape of the heart correction net to some extent without sacrificing the desired properties, and to improve the productivity of the heart correction net. Yet, no practical finding has been obtained regarding suitable simplification of the shape of a heart correction net. Even if the design of a heart correction net can be changed so as to properly simplify the shape, the relation between the heart correction net and the contour of a heart my not be appropriately maintained appropriately. For example, such design change may cause excess constraint to a portion of a heart, or constraining force of the heart correction net with respect to one portion of a heart to be weakened to a considerable extent.

In order to knit a heart correction net that snugly conforms to a patient's heart, a manufacturing method of a heart correction net is preferably provided in which the shape of the heart correction nets is suitably simplified and the productivity of the net is improved.

Means for Solving the Problems

A manufacturing method according to the present invention provides a heart correction net that is fitted to an outside of a heart and inhibits excessive expansion of the heart. The method includes: a first step wherein a direction, in which an apex and a base of the heart are connected, is defined as a layer direction, a cross-sectional image of a cross-section intersecting with the layer direction of the heart is taken with a tomographic device at a plurality of spots spaced apart in the layer direction; a second step wherein an outline of the heart is extracted from each of a plurality of the cross-sectional images taken in the first step; a third step wherein a direction along an outline of the cross-section intersecting with the layer direction of the heart is defined as a circumferential direction, with respect to a three-dimensional shape reconstructed based on a plurality of the outlines extracted in the second step, a dividing point is defined at a plurality of spots spaced apart in the circumferential direction; a fourth step wherein, based on a plurality of the dividing points defined in the third step, a contour of the heart in three-dimension is divided into divided regions, each of the divided regions is surrounded by dividing lines connecting the plurality of the dividing points, while an approximate shape of each of the divided regions is maintained, each of the divided regions is developed on a two-dimensional plane, in which a partial separation between each of the divided regions is tolerated, and development data is created, which includes positional information after development regarding the plurality of the dividing points on the two-dimensional plane; a fifth step wherein, based on the development data created in the fourth step, paper-pattern data is created, which is necessary when the heart correction net is knitted with a computerized knitting machine; and a sixth step wherein, based on the paper-pattern data created in the fifth step, the heart correction net is knitted with the computerized knitting machine.

According to the manufacturing method of the heart correction net constructed as above, in the fourth step, a contour of the heart represented based on a plurality of the dividing points in the three-dimensional space is divided into divided regions, each of the divided region is surrounded by dividing lines connecting the plurality of the dividing points. While an approximate shape of each of the divided regions is maintained, each of the divided regions is developed on a two-dimensional plane. Maintaining the approximate shapes of the divided regions, which is mentioned here, means that slight deformation is tolerated as long as the deformation does not adversely affect the property of the final product of the heart correction net.

For example, when a divided region having a three-dimensional shape is developed on a two-dimensional plane, some kind of deformation is always necessary. If such deformation of the divided region is subtle and does not adversely affect the property of the heart correction net, the deformation is considered to maintain the approximate shape of the divided region. If the divided region is divided smaller, the degree of deformation becomes smaller. Therefore, by fragmenting the divided region as much as necessary to suitably approximate and reproduce the contour of the heart, each divided region can be developed on a two-dimensional plane while the approximate shape of the divided region is maintained.

After developing each divided region on the two-dimensional plane as above, if the paper-pattern data, required when the heart correction net is knitted with the computerized knitting machine, is created based on the development data containing positional information of the dividing points after the development, the paper-pattern data can be more easily prepared after the two-dimensionalization of the dividing points, which is originally three-dimensional data. Therefore, as compared to a case in which paper-pattern data is prepared directly from three-dimensional data, work for preparing paper-pattern data can be reduced, which similarly reduces the manufacturing cost of the heart correction net.

Moreover, when such two-dimensionalization is performed, a plurality of the divided regions is intentionally defined in order to maintain the approximate shape of the each divided region. As a result, the shape of the final product of the heart correction net can be a suitable resemblance/reproduction to/of the contour of the heart. Such heart correction net can sufficiently fit to a patient's heart. In other words, such heart correction net is not simplified in the shape thereof for the purpose of simplifying the paper-pattern data. Therefore, there is no chance for a portion of a heart being excessively constrained by the heart correction net, or for constraining force applied to one portion of the heart in the heart correction net becoming excessively weak.

Moreover, in the manufacturing method according to the present invention, in the fourth step, "a line segment connecting the plurality of the dividing points adjacently disposed along the circumferential direction" is defined as a line segment in the circumferential direction, "a line segment connecting the plurality of the dividing points having a proximate positional relation between the plurality of the outlines adjacently disposed", "a line segment connecting a tip of the apex of the heart and the dividing point disposed on the outline that is located proximate to the apex" are each defined as a line segment in the layer direction, and "quadrangular regions each having vertexes, consisting of four of the plurality of the dividing points, and four sides, consisting of two of a plurality of the line segments in the circumferential direction and two of a plurality of the line segments in the layer direction" and "triangular regions each having vertexes, consisting of two of the plurality of the dividing points and the tip, and three sides, consisting of the line segment in the circumferential direction and two of the plurality of the line segments in the layer direction" are defined as the divided regions, wherein, when the divided regions are developed on a two-dimensional plane, the quadrangular divided regions are each developed into a isosceles trapezoidal shape, whereas the triangular divided regions are each developed into an isosceles triangular shape, and wherein, in the divided regions each having the isosceles trapezoidal shape, the plurality of the line segments in the circumferential direction is changed so as to be parallel to a lateral axis of the two-dimensional plane, lengths of the plurality of the line segments in the circumferential direction remain to be identical with lengths of the plurality of the line segments in the circumferential direction prior to the development, and a height of the isosceles trapezoidal shape is changed to an average length of the plurality of the line segments in the layer direction prior to the development, whereas, in the divided regions each having the isosceles triangular shape, the line segment in the circumferential direction is changed so as to be parallel to the lateral axis of the two-dimensional plane, a length of the line segment in the circumferential direction remains to be identical with the length of the line segment in the circumferential direction prior to the development, and a height of the isosceles triangular shape is changed to the average length of the plurality of the line segments in the layer direction prior to the development. Such method is preferably employed.

In such manufacturing method, when the divided regions are developed, all the line segments of the respective divided regions in the circumferential direction can be aligned in a direction parallel to the lateral axis of the two-dimensional plane. In addition, knitting of the heart correction net with the computerized knitting machine becomes easy. Furthermore, the lengths in the circumferential direction, corresponding to the respective outlines, can be similarly maintained in the heart correction net.

Moreover, in the manufacturing method of the heart correction net according to the present invention, in the fourth step, while an entire length in the circumferential direction is maintained, further correction is performed in the circumferential direction so that a range, corresponding to an anterior surface of the heart, and a range, corresponding to a posterior surface of the heart, become isometric by enlarging/reducing the respective ranges in the circumferential direction.

In such manufacturing method, the range, corresponding to the anterior surface of the heart, and the range, corresponding to the posterior surface of the heart, can be isometric, which makes preparation of the paper-pattern data easy. Moreover, knitting the heart correction net with the computerized knitting machine becomes easy, and knitting can be done in a neat manner.

Furthermore, in the manufacturing method of the heart correction net according to the present invention, in the fourth step, while the entire length in the circumferential direction is maintained, further correction is performed so that a range, corresponding to an anterior surface of a right ventricle of the heart, and a range, corresponding to a posterior surface of the right ventricle of the heart, become isometric, a range, corresponding to the anterior surface of a left ventricle of the heart, and a range, corresponding to the posterior surface of the left ventricle of the heart, become isometric, and a ratio of the lengths in the circumferential direction of a range, corresponding to the right ventricle of the heart, and a range, corresponding to the left ventricle of the heart, becomes equivalent to the ratio prior to the correction, the correction is performed by enlarging/reducing each of the range in the circumferential direction.

In such manufacturing method, the boundaries of the anterior surface of the right ventricle, the posterior surface of the right ventricle, the anterior surface of the left ventricle, and the posterior surface of the left ventricle of the heart can be aligned with the boundaries in the layer direction in the development view. Moreover, knitting the heart correction net with the computerized knitting machine becomes easy, and knitting can be done in a neat manner.

The following describes one example of embodiments according to the present invention with reference to drawings.

EXPLANATION OF REFERENCE NUMERALS

Figure 1:
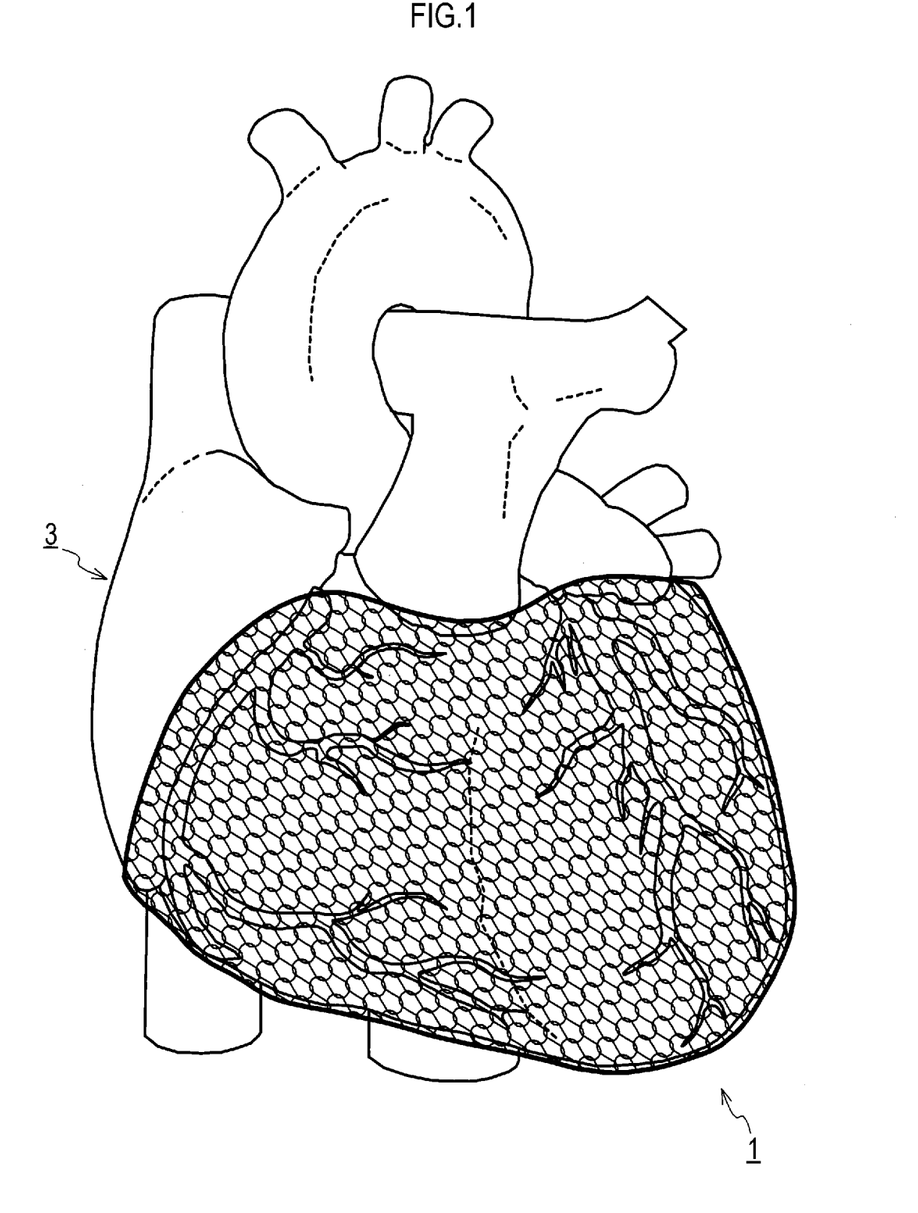
FIG. 1 is a perspective view showing a heart correction net fitted to a heart.

1 . . . heart correction net, 3 . . . heart, 11 . . . nuclear magnetic resonance diagnostic apparatus, 11' . . . multi-detector CT, 12 . . . image processing workstation, 14 . . . echocardiographic apparatus, 20 . . . CAD workstation, 21 . . . CAD workstation for knitting machine, 22 . . . computerized knitting machine for weft knitting Mode for Carrying Out the Invention A heart correction net 1 is a medical equipment, as shown in FIG. 1, that is fitted to the outside of a heart 3 and inhibits the heart 3 from excessively expanding. This heart correction net 1 is knitted by a computerized knitting machine that is capable of knitting a knitting thread into a multidimensional shape. Specifically, the heart correction net 1 is formed by taking images of the multidimensional shape of the heart 3 of each patient with a tomographic apparatus, such as MRI, and by using paper-pattern data created based on the tomographic images.

The shape of the heart correction net 1 consequently coincides with the multidimensional shape of the heart 3, which snugly conforms to the heart 3 of each patient irrespective of the size and shape differences. It is to be noted that, although knitted fabric of the heart correction net 1 is illustrated so as to have tetragonal stitches in FIG. 1, this is merely descriptive for simplification of the drawing and does not show any specific shape of the actual stitches.

Now, a system for manufacturing the heart correction net 1 will be explained.

Figure 2:
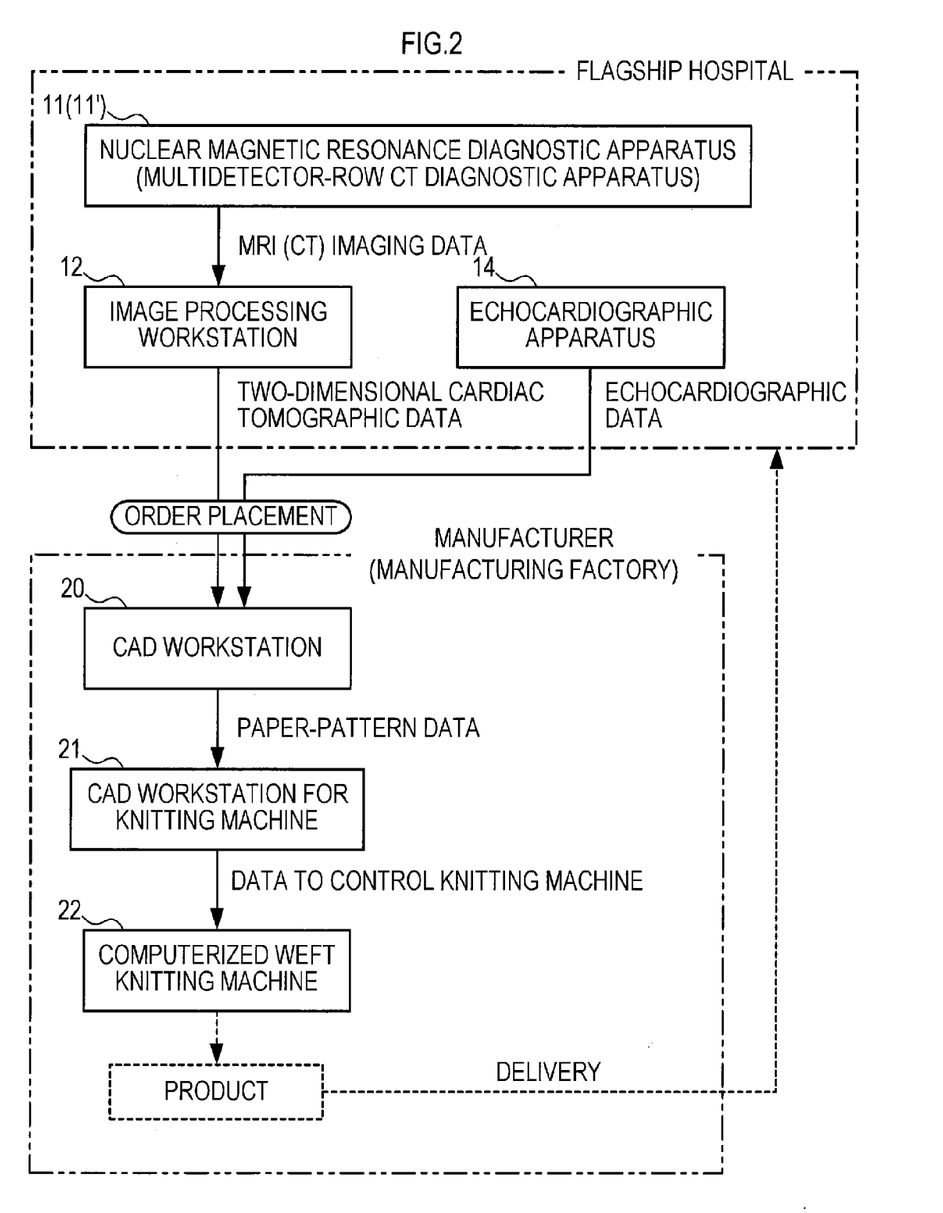
FIG. 2 is an explanatory view showing a manufacturing system of the heart correction net.

The manufacturing system of the heart correction net 1 includes, as shown in FIG. 2, a nuclear magnetic resonance diagnostic apparatus 11 (to be also referred to as MRI 11) (or to be alternatively referred to as a multi-detector CT 11') (to be also referred to as MDCT 11'), an image processing workstation 12 (to be also referred to as a workstation 12), an echocardiographic apparatus 14 (to be also referred to as an examination apparatus 14), a CAD workstation 20 (to be also referred to as a workstation 20), a CAD workstation for knitting 21 (to be also referred to as a workstation 21), and a computerized knitting machine for weft knitting 22 (to be also referred to as a knitting machine 22).

In this system, the MRI 11 (or MDCT 11'), the workstation 12, and the examination apparatus 14 are installed at flagship hospitals, from which orders for the heart correction net 1 are placed, whereas the workstation 20, the workstation 21, and the knitting machine 22 are installed at a manufacturer (at a manufacturing factory) of the heart correction net 1.

As commonly known, the MRI 11 takes tomographic images of human bodies with nuclear magnetic resonance, and the MDCT 11' takes tomographic images of human bodies with x-rays. Either of the MRI 11 and the MDCT 11' may be employed.

The workstation 12 performs data processing with respect to tomographic imaging data (MRI scan data or contrast enhanced CT data) taken by the MRI 11 (or the MDCT 11'). In the present embodiment, cardiac tomographic data (cardiac MRI imaging data or cardiac CT images) in end-diastole and end-systole is extracted in the workstation 12. It is to be noted that, in the present embodiment, 30 images/second are taken in the imaging process, and that the data in the end-diastole is specified in electrocardiographic data and only the imaging data in the end-diastole is extracted.

The examination apparatus 14 exams the configuration of a heart based on the reflection of ultrasonic waves, and obtains more accurate configuration of the heart when used together with the MRI 11 (or the MDCT 11'). Moreover, by using the examination apparatus 14 and accurately diagnosing the clinical condition of each patient with mitral insufficiency, diagnosis can be made whether a treatment with the heart correction net 1 is applicable. Moreover, the amount of reefing of a mitral valve with the heart correction net 1 and the amount of reefing in the short diameter of a heart with the heart correction net 1 in the papillary muscle level can be determined.

The workstation 20 performs data processing based on data sent from the workstation 12 and the examination apparatus 14. The workstation 20 includes data processing software, such as three-dimensional image construction software, general-purpose CAD software, and paper-pattern creating software.

In the present embodiment, the three-dimensional image construction software in the above-described workstation 20 is utilized so as to conduct a process in which, from thresholds of two-dimensional tomographic data (DICOM data), obtained from the workstation 12, outlines of a heart is extracted for defining dividing points, for developing the data on a plane, and for providing various types of corrections, which will be explained later.

Moreover, in the workstation 20, based on cardiac ultrasonic wave data further obtained from the examination apparatus 14, correction values can be set, for example, for adjusting the amount of reefing. The data that is required for setting correction values includes: left ventricular end-diastolic dimension (LVDd), left ventricular end-systolic dimension (LVDs), long axis dimension of left ventricle, mitral annulus dimension (short diameter, long diameter), adhered position of papillary muscle, deviation amount in the position of mitral valve in systole (which is called tethering or tenting and indicates the vertical distance between a line connecting the anterior and posterior annulus and the leaflet junction of mitral valve), amount of mitral reflux (evaluated in long-axis image), and reflux region (evaluated in short-axis image). By performing correction based on a set of such data, obtained data is corrected to be potentially optimal for each individual case.

Since the shape of the periphery of a heart can be more accurately obtained through calculation with reference to MD-CT images, correction based on echocardiographic data is not performed. Alternatively, measurement is conducted based on the MD-CT images. That is to say that optimal data is constructed by utilizing the advantageous characteristics of the MRI 11 (or MDCT 11') and the examination apparatus 14. Issues, such as whether to conduct correction based on echocardiographic data, if such correction is adopted, the optimal degree of the correction, and so on are cooperatively considered between, for example, a cardiac surgeon and a person in charge of image processing in the manufacturer side. If necessary, such issues can be discussed with an orderer (a cardiac surgeon in the flagship hospital side) so as to eventually complete data that is potentially optimal for each individual case.

In the workstation 20, paper-pattern data is created in which a three-dimensional heart shape, corrected after extraction, is two-dimensionally developed for knitting the heart correction net 1. The workstation 21 controls the knitting machine 22 based on the paper-pattern data in two-dimensions (a bitmap format file) that is transmitted from the workstation 20.

The knitting machine 22 knits a knitting thread into a knitted fabric having a multidimensional shape based on instruction from the workstation 22. In the present embodiment, a computerized weft knitting machine (product name: SWG041, manufactured by SHIMA SEIKI MFG., LTD.) suitable for WHOLEGARMENT (registered trademark) is used as the knitting machine 22.

The knitting thread used herein is made with biocompatible materials. The quality and the thickness of the knitting thread is not particularly limited as long as the materials have properties (such as mechanical strength, chemical strength, and elastic properties) suitable for the intended purpose of the heart correction net 1. One example of such material includes a material made by twisting a single non-absorbable fiber such as polyester, polytetrafluoroethylene, foamed polytetrafluoroethylene (foamed PTFE, ePTFE), polypropylene, polydiethylene fluoride (hexafluoropropylene-vinylidene fluoride), and a material made by twisting a single absorbable fiber such as polyglactin, polyglycolic acid, polyethylene glycol, polylactic acid, polylactide, polyglycolide, polycaprolactone, multianhydride, polyamide, polyurethane, polyester amide, polyorthoester, polydioxane, polyacetal, polyketal, polycarbonate, polyorthoester, polyphosphazen, polyhydroxybutyrate, polyhydroxyvalerate, polyalkyleneoxalate, polyalkylene succinate, poly(methyl vinyl ether), poly(maleic anhydride), poly (amino acid) and copolymers, compounds or mixtures thereof. The material may be combinations of these materials so as to make a hybrid type of thread. Among the knitting thread made with these materials, only one type, or two and more types of thread may be used.

In the above-described system, the MRI 11 (or MDCT 11'), the workstation 12, and the examination apparatus 14 are operated by a cardiac surgeon, cardiologist, or radiologist in a flagship hospital side so that cardiac tomographic data in two-dimension (DICOM data) and echocardiographic data are prepared in the flagship hospital side. The two-dimensional tomographic data and the echocardiographic data are transmitted through a communication line to the manufacturer (the manufacturing factory).

In the manufacturer (manufacturing factory) side, upon receiving the data transmitted from the flagship hospital side, the above-described data processing in the workstation 20 is performed. When two-dimensional knitting data is completed based on the three-dimensional data in the workstation 20, the knitting data is transmitted to the workstation 21.

The workstation 21 and the knitting machine 22 are operated by persons in charge in the manufacturer side. By knitting the thread based on the above-described knitting data, the heart correction net 1 is manufactured so as to have the configuration represented by the knitting data. The manufactured heart correction net 1 is immediately delivered to the flagship hospital and used.

Now, the process from a step of taking sectional images of a heart to a step of knitting a heart correction net will be explained further in detail based on FIG. 3. In the manufacturing of the heart correction net 1, first, cross-sectional images of cross-sections are taken with the MRI 11 (or the MDCT 11') (S1). In S1, in which the direction connecting the apex and the base of the heart (the long axial direction of the heart) is defined as the layer direction, a cross-sectional image of a cross-section, intersecting with the layer direction of the heart, is taken with the MRI 11 at a plurality of spots (eight spots in the present embodiment) spaced apart in the layer direction.

Subsequently, from the cross-sectional images taken in S1 at a plurality of spots (eight spots in the present embodiment), outlines of the heart are respectively extracted with the workstation 20 (S2). With respect to a three-dimensional shape, reconstructed based on the outlines extracted in S2, a plurality of dividing points (16 points in the present embodiment) are defined (S3), in which a direction along the outline of a cross-section intersecting with the above-mentioned layer direction of the heart is defined as a circumferential direction. The dividing points are disposed on the outlines and spaced apart in the circumferential direction.

Figure 4:
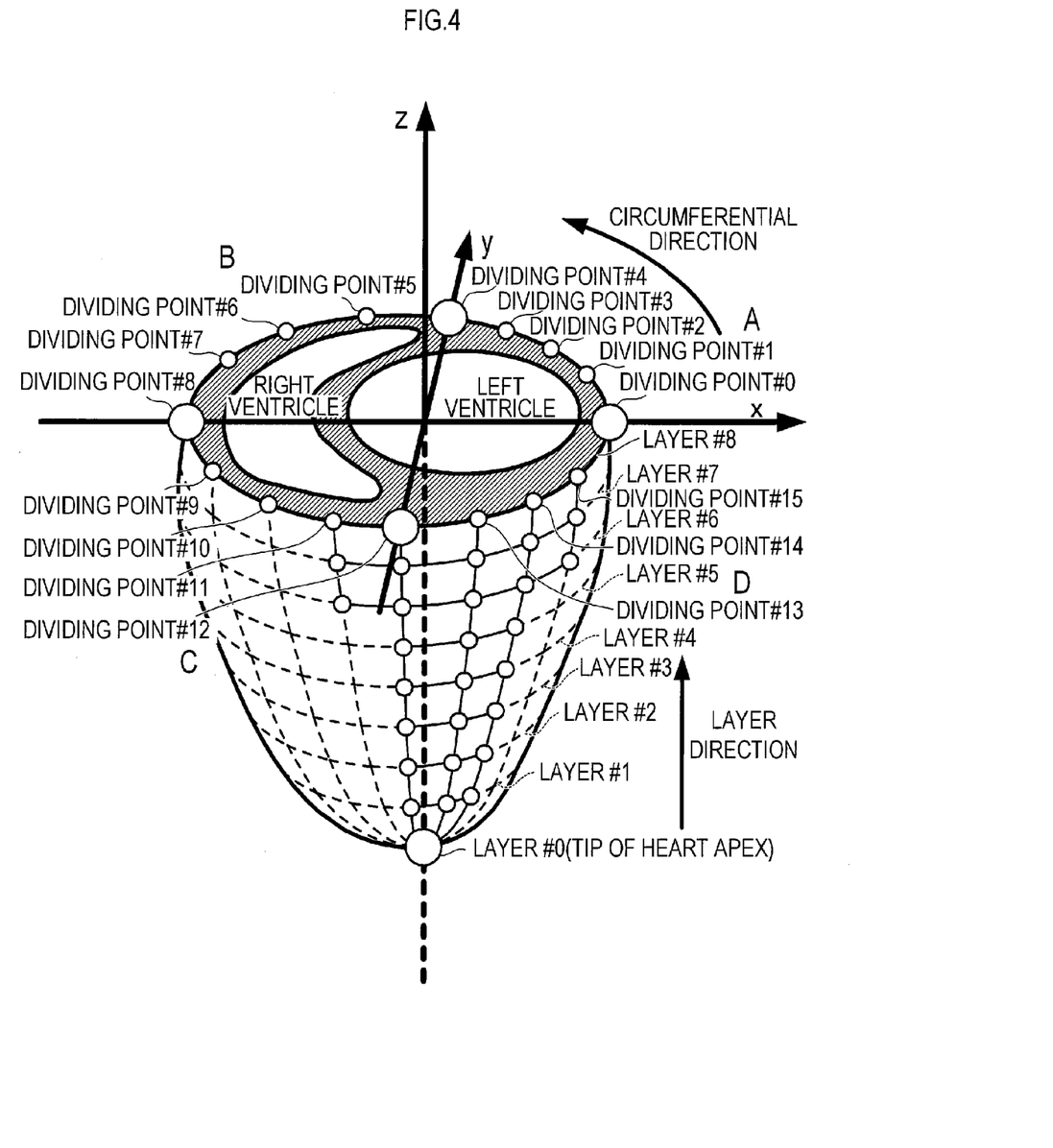
FIG. 4 is an explanatory view showing dividing points, dividing lines, and divided region defined on a heart.

A schematic diagram is shown in FIG. 4 which shows the outlines extracted in S2 and the dividing points defined in S3. In the example shown in FIG. 4, a coordinate system is defined while the cross-sections of the heart are viewed from above. The x-axis extends in the long axial direction of the cross-section, and the positive direction of the x-axis direction is defined toward the left ventricle and the negative direction is defined toward the right ventricle. On the other hand, the y-axis extends in the short axial direction of the cross-section, and the positive direction of the y-axis is defined toward the posterior surface of the heart and the negative direction is defined toward the anterior surface of the heart. Furthermore, according to the right-handed system, the positive direction of the z-axis is directed upward. According to this coordinate system, various setting and conversion of coordinates are conducted.

Moreover, in the case of the present embodiment, the positions of layers #1 to #8 shown in FIG. 4 are image-taking positions for cross-sections. The eight outlines extracted in S2 are extracted from the cross-sectional images taken at these image-taking positions. The respective positions (of layers #1 to #8) in the layer direction are aligned from the layer #0, which is the point of origin disposed on the tip of the apex of the heart, in the order of layer #1 to #8 toward the base of the heart.

Furthermore, in the case of the present embodiment, the dividing points are defined in S3 so that 16 points are defined on each of the outlines. The dividing points are defined on each of the outlines in a counterclockwise around the z-axis along the outlines in the order of the dividing points #0 to #15. More specifically, in the case of the present embodiment, the dividing points #0 and #8 are disposed on the intersecting points of the cross-section and the x-axis (that is, on the both end positions in the long diameter of the cross-section of the heart), which are shown in the figure. The dividing points #4 and #12 are defined on a boundary between the left ventricle and the right ventricle. In FIG. 4, although the y-axis is shown so as to extend via the dividing points #4 and #12, it is only for convenience of illustration and the boundary between the left ventricle and the right ventricle are not necessarily located on the y-axis. The dividing points #4 and #12 may be disposed away from the y-axis.

The remaining dividing points #1 to #3, #5 to #7, #9 to #11, #13 to #15 are arbitrarily disposed so as to be spaced apart as much as necessary to represent the contour of a heart. A larger number of the dividing points can more accurately represents the contour of a heart, which, however, increases the amount of data. The number of dividing points is preferably kept within a range necessary to represent the feature of the contour of the heart without increase the number to an excessive extent. From this aspect, three dividing points are respectively disposed between the above-described dividing points #0, #4, #8, #12 in the present embodiment. As a result, 16 dividing points are disposed on each of the outlines.

When the above-described dividing points (in the present embodiment, 16 points×8 layers) are defined, based on the dividing points defined in S3, the three-dimensional contour of the heart is divided into a plurality of divided regions, each of which is surrounded by dividing lines connecting the dividing points along the surface of the heart, and the divided regions are developed on a two-dimensional plane (S4).

It is to be noted that, in the following description, a line segment connecting the plurality of the dividing points adjacently disposed along the circumferential direction is referred to as a line segment in the circumferential direction. The line segment in the circumferential direction is disposed on a position so as to substantially coincide with the above-described outline. In addition, a line segment connecting the plurality of the dividing points having a proximate positional relation between the plurality of the outlines adjacently disposed, and a line segment connecting the tip of the apex of the heart and the dividing point disposed on the outline located proximate to the apex are each referred to as a line segment in the layer direction.

The divided regions become either one of quadrangular regions, each having vertexes, consisting of four dividing points, and four sides, consisting of two line segments in the circumferential direction and two line segments in the layer direction, or triangular regions, each having vertexes, consisting of two dividing points and the tip, and three sides, consisting of one line segment in the circumferential direction, and two line segments in the layer direction.

Figure 5A:
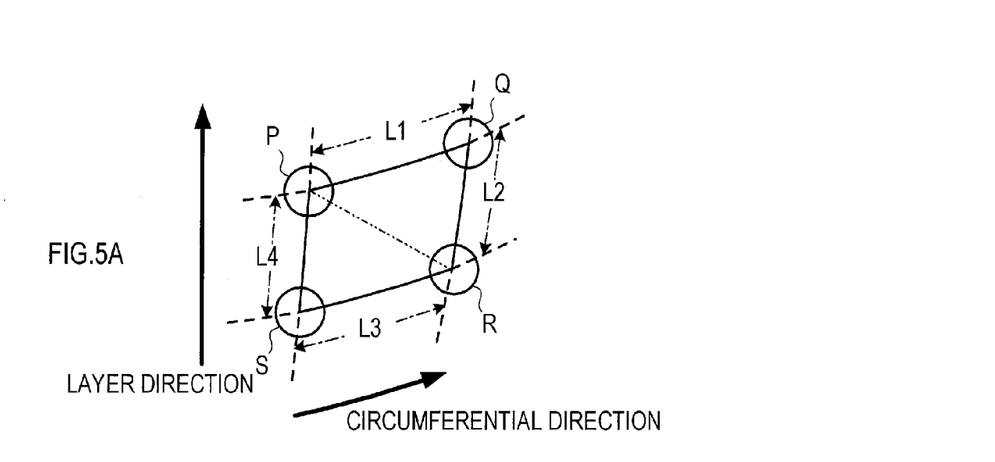
FIG. 5A is an explanatory view showing an example of one divided region disposed in three-dimensional space, FIG. 5B an explanatory view showing a state in which the divided region shown in FIG. 5A is developed into an isosceles trapezoid on a two-dimensional plane.
Figure 5B:
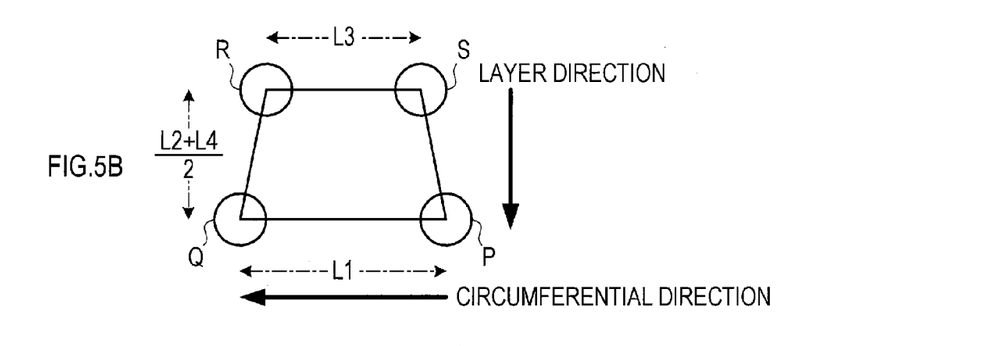

In S4, when the divided regions are developed on a two-dimensional plane, quadrangular divided regions are respectively developed into divided regions in isosceles trapezoidal shapes on the two-dimensional plane. To explain more in detail, one example is shown in FIG. 5A, in which a quadrangular divided region PQRS, defined by the dividing points P, Q, R, and S, has four sides L1, L2, L3, and L4. These four points in three-dimensional space do not often exist in a same plane. Usually, a triangle PQR and a triangle PRS exist on separate planes that intersect with the line segment PR. Therefore, in the present invention, coordinate transformation is performed so as to approximate the shape of the divided region PQRS with an isosceles trapezoid and to develop the approximated shape on a two-dimensional plane. Specifically, when the above-described divided region PQRS is transformed into an isosceles trapezoid, as shown in FIG. 5B, the line segments in the circumferential direction PQ and SR are changed so as to be parallel to the lateral axis of the two-dimensional plane, the lengths L1 and L3 of the respective line segments in the circumferential direction PQ and RS remain to be the identical lengths L1 and L3 of the line segments in the circumferential direction PQ and RS prior to the development, and the height of the isosceles trapezoid is changed to the average length of the line segments in the layer direction L2 and L4 prior to the development, i.e., (L2+L4)/2. In S4, the divided regions in triangular shapes are developed into divided regions in isosceles triangular shapes on a two-dimensional plane. This corresponds to a case in which the length of the upper base of the above-described isosceles trapezoid is zero. Therefore, the triangular shape is transformed into an isosceles triangle in the same manner as in the case of isosceles trapezoid.

Figure 5C:
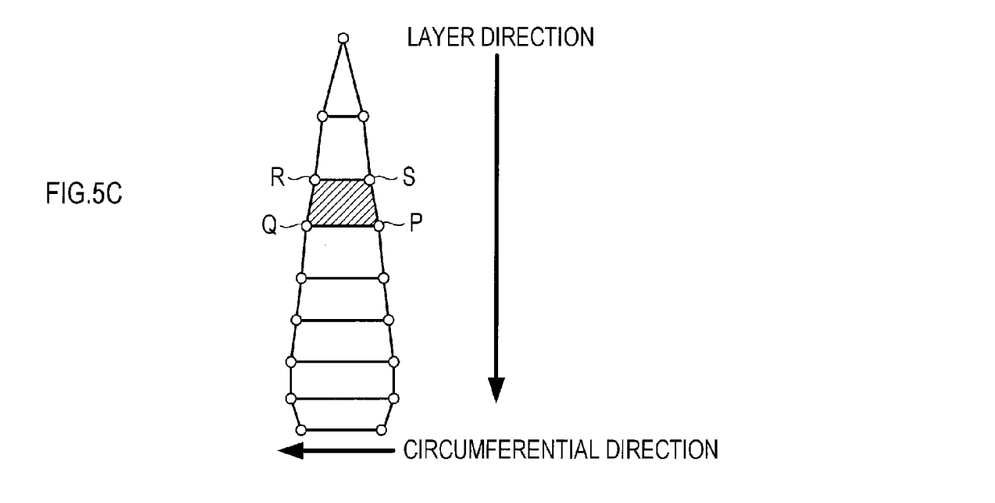
FIG. 5C is an explanatory view showing one row of the divided regions aligned in a layer direction.
Figure 6A:
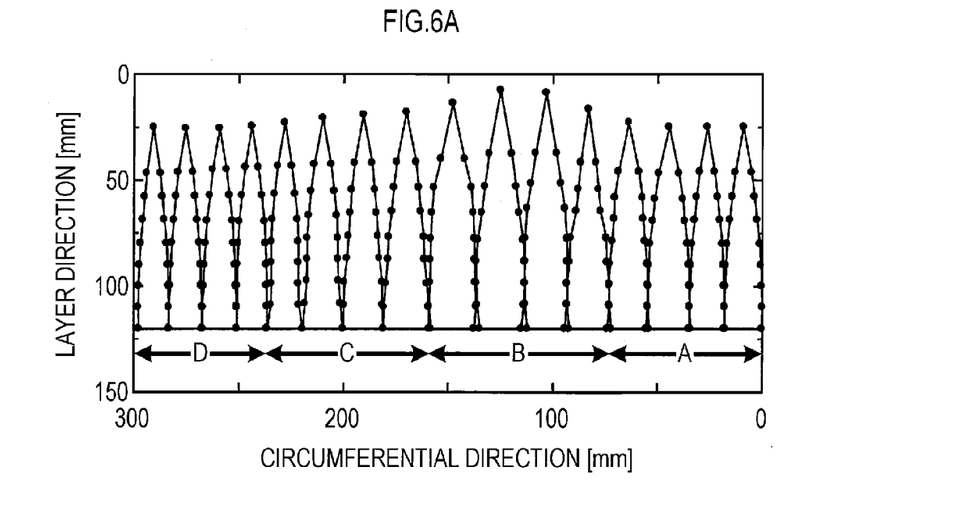
FIG. 6A is a development view showing all the divided regions.

FIG. 5C shows an example of divided regions transformed into an isosceles trapezoid or an isosceles triangle by the above-described technique. In the present embodiment, such divided regions are aligned in the layer direction making 16 rows. FIG. 6A shows all the 16 rows of the divided regions.

The ranges shown with A, B, C, and D in FIG. 6A respectively correspond to the ranges A, B, C, and D in FIG. 4. The range A corresponds to the contour of the rear surface of the left ventricle developed on a two-dimensional plane. Similarly, the range B corresponds to the posterior surface of the right ventricle, the range C corresponds to the anterior surface of the right ventricle, and the range D corresponds to the anterior surface of the left ventricle respectively.

The 16 rows of the divided regions shown in FIG. 6A are divided regions developed on a two-dimensional plane, in which a separation created between each of the divided regions along the line segment in the layer direction is tolerated and an approximate shape of each divided region is maintained.

Figure 6B:
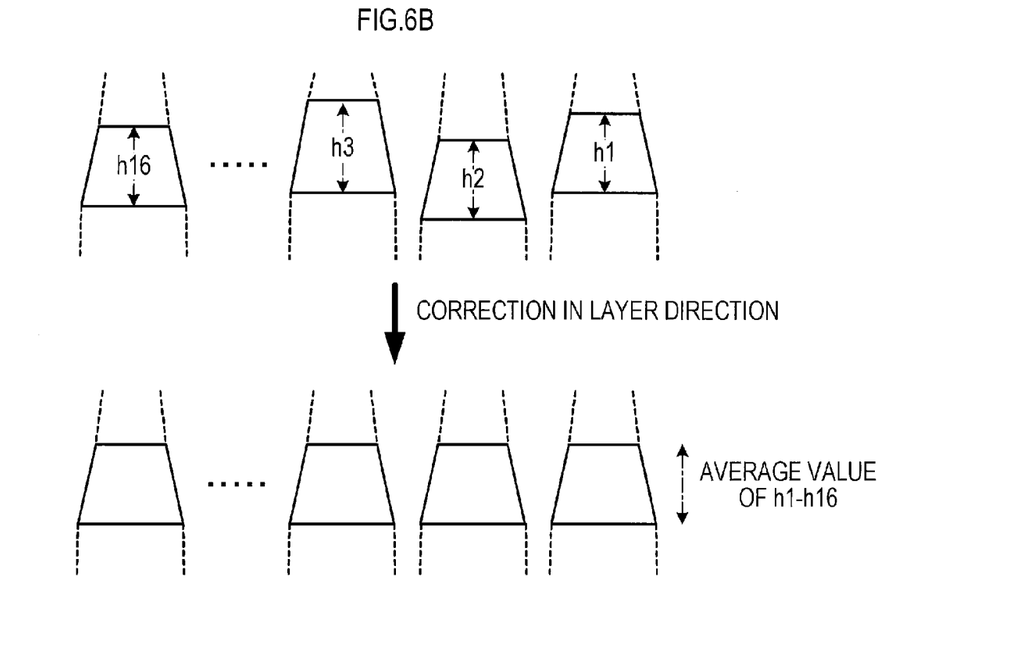
FIG. 6B is an explanatory view showing a technique for correction in the layer direction.

When development is performed in the manner shown in FIG. 6A, the length of each divided region in the 16 rows in the layer direction becomes different in each row. Therefore, in S4, correction is performed in the layer direction so as to make lengths of the divided regions of the 16 rows in the layer direction become uniform. Specifically, as shown in FIG. 6B, among the 16 rows of divided regions, 16 divided regions disposed on an equivalent level in the layer direction are subjected to coordinate transformation in which an average of the lengths h1 to h16 in the layer direction is obtained and the respective divided regions are accordingly enlarged/reduced in the layer direction. A development view after such coordinate transformation is shown in FIG. 7A.

Figure 7A:
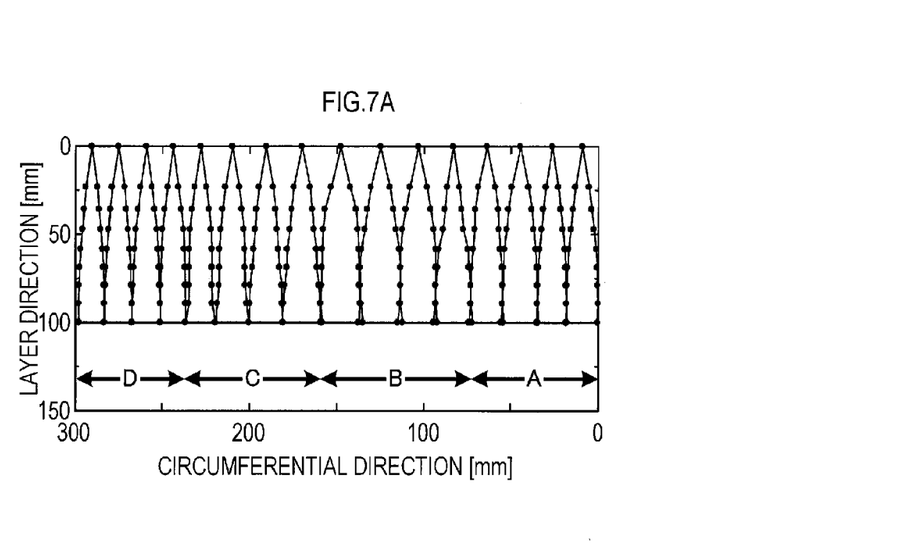
FIG. 7A is a development view showing a state after correction in the layer direction.
Figure 7B:
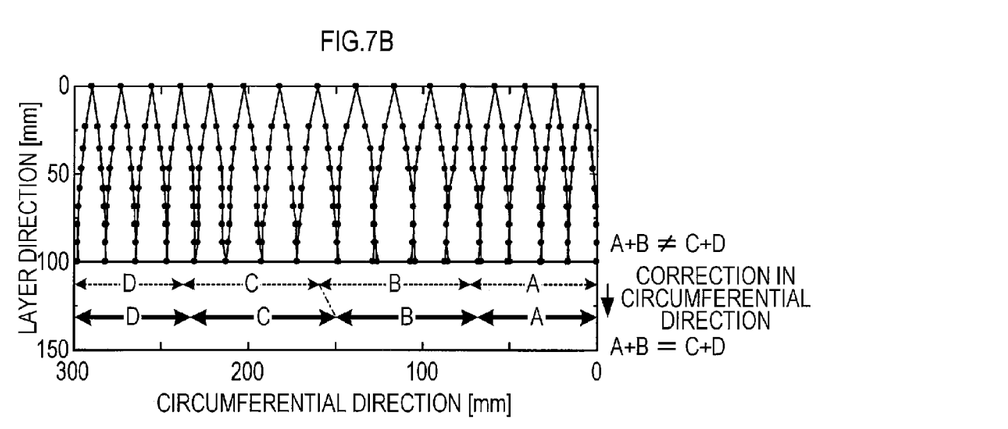
FIG. 7B is a development view showing a state after correction in a circumferential direction.

As clearly shown in FIG. 7A, after transformation in the layer direction is performed, the lengths of the respective divided regions in 16 rows in the layer direction become uniform. Consequently, the entire lengths of the respective rows, each having eight layers, also become uniform. After such correction in the layer direction, correction in the circumferential direction is further performed. Specifically, as shown in FIG. 7B, a first correction in the circumferential direction is performed in which, while the entire length in the circumferential direction is maintained, coordinates are transformed by enlarging/reducing respective ranges so that the lengths of the ranges C+D, corresponding to the anterior surface of the heart, and the ranges A+B, corresponding to the posterior surface of the heart, become isometric. In the case of the example shown in FIG. 7B, the ranges C+D, corresponding to the anterior surface of the heart is enlarged, whereas the ranges A+B, corresponding to the posterior surface of the heart, is reduced. As a result, the boundary between the range B and the range C is brought to the middle point of the entire length in the circumferential direction.

After such correction, a second correction in the circumferential direction is performed in which, while the entire length in the circumferential direction is maintained, coordinates are transformed by enlarging/reducing the respective ranges in the circumferential direction so that the range C, corresponding to the anterior surface of the right ventricle of the heart, and the range B, corresponding to the posterior surface of the right ventricle of the heart, become isometric, the range D, corresponding to the anterior surface of the left ventricle of the heart, and the range, corresponding to the posterior surface of the left ventricle A of the heart, become isometric, and the ratio of the lengths in the circumferential direction of the ranges B+C, corresponding to the right ventricle of the heart, and the ranges A+D, corresponding to the left ventricle of the heart, becomes equivalent to the ratio prior to the enlarging/reducing correction in the circumferential direction (at the point in time shown in FIG. 6A or FIG. 7A).

Figure 8A:
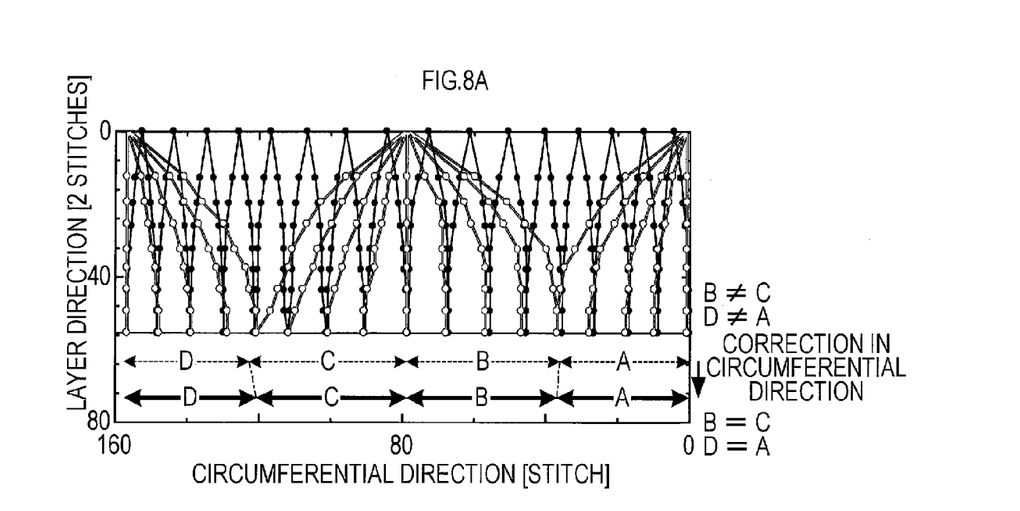
FIG. 8A is a development view showing a state after further correction and a state in which correction is added for preparing paper-pattern data.

Due to such correction, the divided regions in the 16 rows are respectively formed as shown with black lines in FIG. 8A, in which the ranges B and C become isometric, and the ranges A and D also become isometric. Moreover, with respect to the ranges B+C and the ranges A+D, the ratio of the lengths in the circumferential direction become equivalent to the ratio prior to the correction.

At this point in FIG. 8A, the isosceles trapezoidal divided regions, respectively having lower bases that are shorter than upper bases, are processed similarly to isosceles trapezoidal divided regions having equivalent lengths of the lower and upper bases. This is because the ability of the heart correction net to fit to a heart decreases if the opening portion of the final product has a narrowing shape. In other words, since the opening portion of a heart correction net is to be placed proximate to the base of a heart, if the heart correction net needs to be fitted exactly to the contour of the heart, the circumferential length of the heart correction net becomes shorter than the maximum circumferential length of the heart, which makes it difficult for the heart correction net to pass through the maximum circumferential portion of the heart. Therefore, in the present embodiment, by making the lengths of the above-described lower bases equivalent to the lengths of the upper bases, the opening portion of the heart correction net is enlarged and the ability to fit to a heart is improved. It is to be noted that such enlargement is made only in one portion in the side of the base, and that, in the range from the maximum circumferential portion of a heart to the apex of the heart, the heart correction net can be easily fitted to the outer surface of a heart without any problems.

Figure 3:
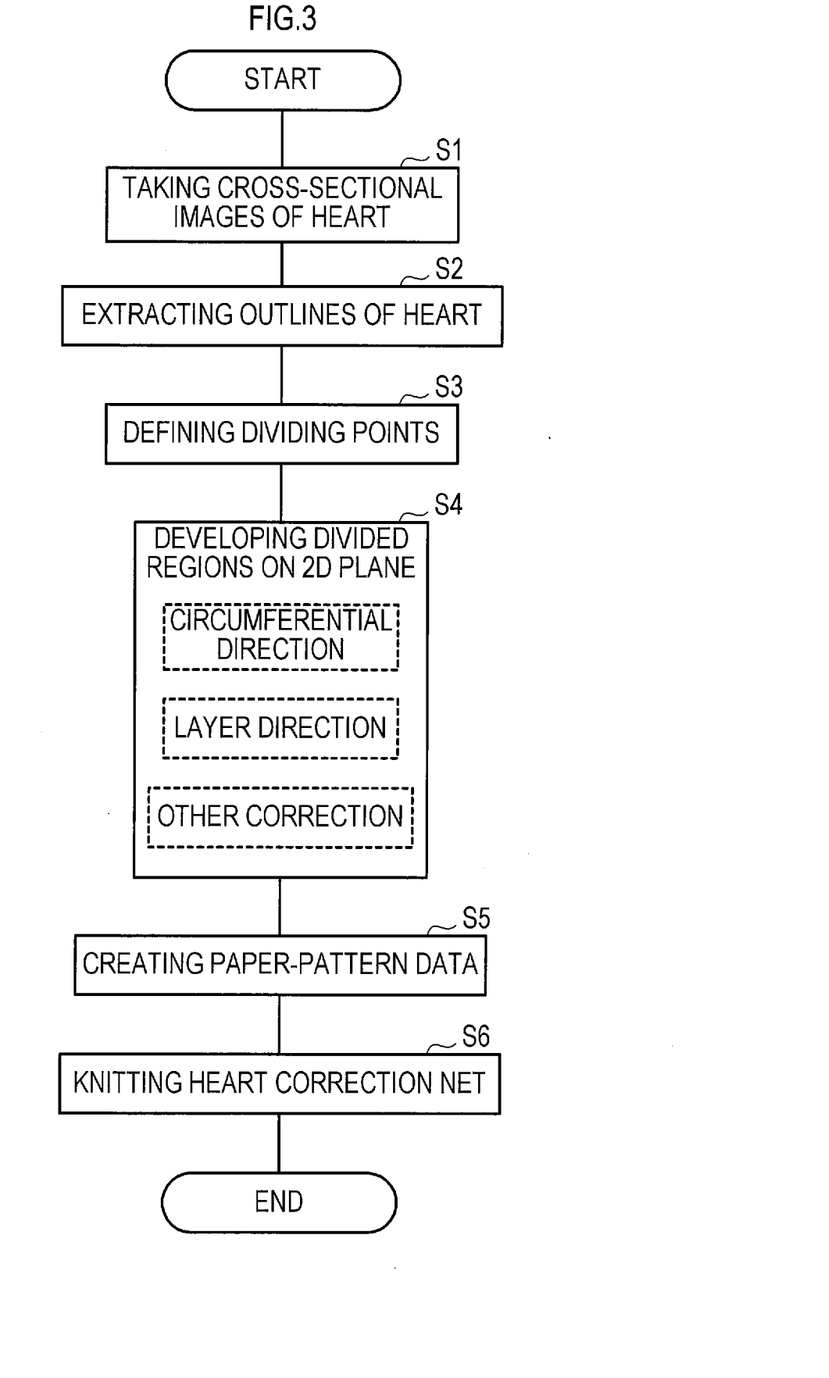
FIG. 3 is a flowchart showing a manufacturing method of the heart correction net.

When S4, shown in FIG. 3, is completed as described above, paper-pattern data is subsequently created (S5). In S5, based on the development data shown with black lines in FIG. 8A, conversion is conducted for an input to the knitting machine 22, in which coordinates are transformed in a manner shown with double lines in FIG. 8A. Specifically, the double lines fill up a gap between each row by gathering the coordinates shown with black lines to the dividing points #0 and #8 in the circumferential direction.

Moreover, in FIG. 8A, numeric conversion is performed both in the circumferential direction and the layer direction so that the number of knitting stitches becomes a unit of measurement. The length in millimeter of one stitch varies depending on the type of a knitting thread and gauges (the interval between knitting needles) of a knitting machine. A sample of an actual net is made so as to obtain the scales in the circumferential direction and the layer direction. The relation between the number of stitches and the length is specified, for example, 1.9 mm/stitch in the circumferential direction and 0.9 mm/stitch in the layer direction.

Figure 8B:
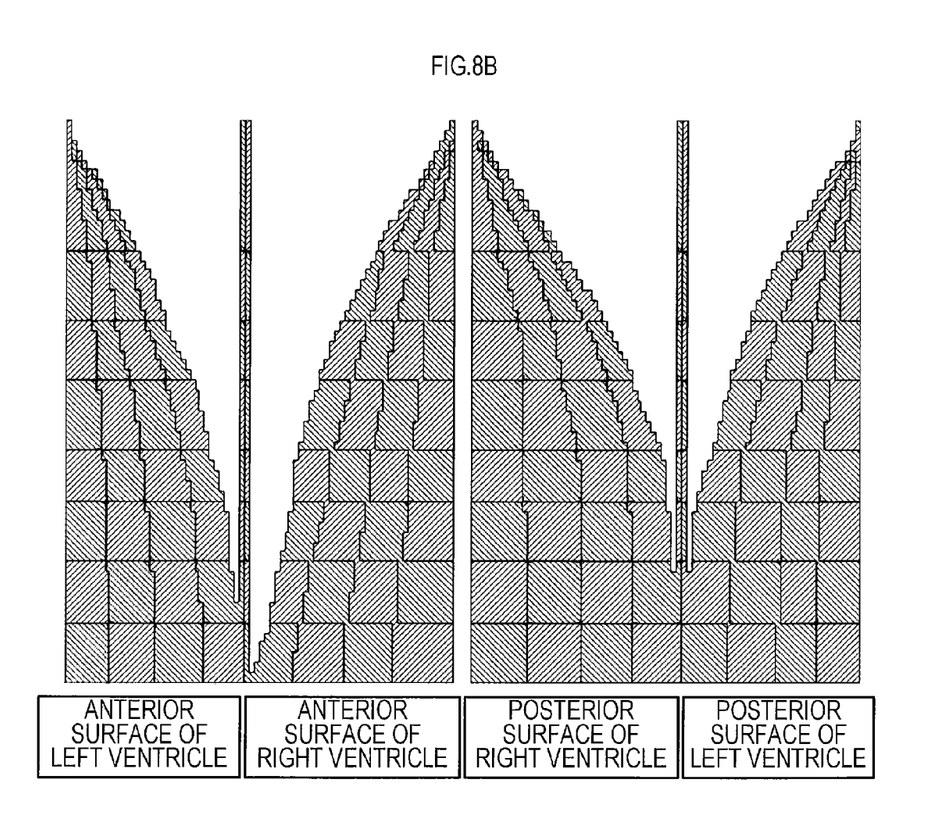
FIG. 8B is an explanatory view showing an image represented based on paper-pattern data, in which one stitch corresponds to one dot.

One example of the paper-pattern data created as above is shown in FIG. 8B. In FIG. 8B, although the regions in different colors are shown with different hatchings for convenience of illustration, the original image is a bitmap image in which one dot corresponds to one knitting stitch. The linear portion, extending in the layer direction between the posterior surface of the left ventricle and the posterior surface of the right ventricle, and the linear portion, extending in the layer direction between the anterior surface of the left ventricle and the anterior surface of the right ventricle, are both added for convenience in order to knit the boundary between the range A and range B and the boundary between the range C and the range D.

When the paper-pattern data is created as described above, the paper-pattern data is provided (inputted) to the knitting machine 22 so as to knit a heart correction net (S6). As a result, a heart correction net, having the shape according to the paper-pattern data, is knitted.

The heart correction net knitted here does not completely conform to the contour of the heart in a strict sense, since the shapes of individual dividing regions are slightly corrected. However, as compared to the technique disclosed in the above-described Patent Document 1, the shape of the heart correction net is particularly similar to the shape of a patient's heart. Therefore, the effect is expected to be the same as the effect of the technique disclosed in the above-described Patent Document 2. Moreover, as compared to a case in which the contour of a heart is completely reproduced, the slight correction with respect to the shapes of the individual dividing regions can make the shape of the paper-pattern data, created in S5, remarkably simplified, which can also reduce the amount of data processing necessary for manufacturing a heart correction net. Therefore, the practical advantage becomes extremely large.

Although the above explained the embodiment according to the present invention, the present invention is not limited to one particular embodiment described above. The present invention may be carried out in various ways.

For example, in the above-described embodiment, outlines of eight layers are extracted and 16 dividing points are defined on each of the outlines. The number of outlines to be extracted, and the number of dividing points to be defined, for example, may be arbitrary determined respectively.

Moreover, in the above-described embodiment, correction in the circumferential direction and correction in the layer direction are performed in order to improve the productivity. If, for example, no problem is caused by the manufacturing process being complicated, paper-pattern data may be created from the development view shown in FIG. 6A, or from the development view shown in FIG. 7A in which only the correction in the layer direction is performed.

Furthermore, if no problem is cased with the conformity of the shapes, paper-pattern data obtained after correction, which is shown in FIG. 8A, may be directly created from the lengths of the line segments in the circumferential direction and the lengths of the line segments in the layer direction respectively.

The invention claimed is:

1. A manufacturing method of a heart correction net that is fitted to an outside of a heart and inhibits excessive expansion of the heart, the method comprising:
    a first step wherein a direction, in which an apex and a base of the heart are connected, is defined as a layer direction, a cross-sectional image of a cross-section intersecting with the layer direction of the heart is taken with a tomographic device at a plurality of spots spaced apart in the layer direction;
    a second step wherein an outline of the heart is extracted from each of a plurality of the cross-sectional images taken in the first step;
    a third step wherein a direction along an outline of the cross-section intersecting with the layer direction of the heart is defined as a circumferential direction, with respect to a three-dimensional shape reconstructed based on a plurality of the outlines extracted in the second step, a dividing point is defined at a plurality of spots spaced apart in the circumferential direction;
    a fourth step wherein, based on a plurality of the dividing points defined in the third step, a contour of the heart in three-dimension is divided into divided regions, each of the divided regions is surrounded by dividing lines connecting the plurality of the dividing points, while an approximate shape of each of the divided regions is maintained, each of the divided regions is developed on a two-dimensional plane, in which a partial separation between each of the divided regions is tolerated, and development data is created, which includes positional information after development regarding the plurality of the dividing points on the two-dimensional plane;
    a fifth step wherein, based on the development data created in the fourth step, paper-pattern data is created, which is necessary when the heart correction net is knitted with a computerized knitting machine; and
    a sixth step wherein, based on the paper-pattern data created in the fifth step, the heart correction net is knitted with the computerized knitting machine.

2. The method of manufacturing the heart correction net according to claim 1,
    wherein, in the fourth step, "a line segment connecting the plurality of the dividing points adjacently disposed along the circumferential direction" is defined as a line segment in the circumferential direction, "a line segment connecting the plurality of the dividing points having a proximate positional relation between the plurality of the outlines adjacently disposed" and "a line segment connecting a tip of the apex of the heart and the dividing point disposed on the outline that is located proximate to the apex" are each defined as a line segment in the layer direction, and "quadrangular regions each having vertexes, consisting of four of the plurality of the dividing points, and four sides, consisting of two of a plurality of the line segments in the circumferential direction and two of a plurality of the line segments in the layer direction" and "triangular regions each having vertexes, consisting of two of the plurality of the dividing points and the tip, and three sides, consisting of the line segment in the circumferential direction and two of the plurality of the line segments in the layer direction" are defined as the divided regions,
    wherein, when the divided regions are developed on a two-dimensional plane, the quadrangular divided regions are each developed into an isosceles trapezoidal shape, whereas the triangular divided regions are each developed into an isosceles triangular shape, and
    wherein, in the divided regions each having the isosceles trapezoidal shape, the plurality of the line segments in the circumferential direction is changed so as to be parallel to a lateral axis of the two-dimensional plane, lengths of the plurality of the line segments in the circumferential direction remain to be identical with lengths of the plurality of the line segments in the circumferential direction prior to the development, and a height of the isosceles trapezoidal shape is changed to an average length of the plurality of the line segments in the layer direction prior to the development, whereas, in the divided regions each having the isosceles triangular shape, the line segment in the circumferential direction is changed so as to be parallel to the lateral axis of the two-dimensional plane, a length of the line segment in the circumferential direction remains to be identical with the length of the line segment in the circumferential direction prior to the development, and a height of the isosceles triangular shape is changed to the average length of the plurality of the line segments in the layer direction prior to the development.

3. The manufacturing method of the heart correction net according to claim 2,
wherein, in the fourth step, while an entire length in the circumferential direction is maintained, further correction is performed in the circumferential direction so that a range, corresponding to an anterior surface of the heart, and a range, corresponding to a posterior surface of the heart, become isometric by enlarging/reducing the respective ranges in the circumferential direction.

4. The manufacturing method of the heart correction net according to claim 3,
wherein, in the fourth step, while the entire length in the circumferential direction is maintained, further correction is performed so that a range, corresponding to an anterior surface of a right ventricle of the heart, and a range, corresponding to a posterior surface of the right ventricle of the heart, become isometric, a range, corresponding to the anterior surface of a left ventricle of the heart, and a range, corresponding to the posterior surface of the left ventricle of the heart, become isometric, and a ratio of the lengths in the circumferential direction of a range, corresponding to the right ventricle of the heart, and a range, corresponding to the left ventricle of the heart, becomes equivalent to the ratio prior to the correction, the correction is performed by enlarging/reducing each of the ranges in the circumferential direction.

* * * * *